United States Patent [19]

Wypych et al.

[11] Patent Number: 5,188,589
[45] Date of Patent: Feb. 23, 1993

[54] TEXTURED IRRIGATING SLEEVE

[75] Inventors: Peter Wypych, Irvine; Stephen W. Haines, Santa Ana, both of Calif.

[73] Assignee: Alcon Surgical, Inc., Fort Worth, Tex.

[21] Appl. No.: 774,406

[22] Filed: Oct. 10, 1991

[51] Int. Cl.$^5$ .............................................. A61B 17/20
[52] U.S. Cl. ............................... 604/22; 128/24 AA
[58] Field of Search ............ 604/22, 240; 128/24 AA; 606/159, 169–171

[56] References Cited

U.S. PATENT DOCUMENTS

| | | | |
|---|---|---|---|
| 3,589,363 | 6/1971 | Banko et al. | 604/22 |
| 3,659,607 | 5/1972 | Banko | 604/22 |
| 3,693,613 | 9/1972 | Kelman | 604/22 |
| 4,180,074 | 12/1979 | Murry et al. | 128/24 AA |
| 4,223,676 | 9/1980 | Wuchinich et al. | 404/22 |
| 4,515,583 | 5/1985 | Sorich | 609/22 |
| 4,573,979 | 3/1986 | Blake | 604/240 |
| 4,578,059 | 3/1986 | Fabricant et al. | 604/43 |
| 4,609,368 | 9/1986 | Dotson, Jr. | 604/22 |
| 4,634,420 | 1/1987 | Spinosa et al. | 604/22 |
| 4,643,717 | 2/1987 | Cook et al. | 604/22 |
| 4,652,255 | 3/1987 | Martinez | 604/27 |
| 4,681,561 | 7/1987 | Hood et al. | 604/22 |
| 4,705,500 | 11/1987 | Reimels et al. | 604/35 |
| 4,787,889 | 11/1988 | Steppe et al. | 604/22 |
| 4,808,154 | 2/1989 | Freeman | 604/22 |
| 4,816,017 | 3/1989 | Hood et al. | 604/22 |
| 4,816,018 | 3/1989 | Parisi | 604/22 |
| 4,869,715 | 9/1989 | Sherburne | 604/22 |
| 4,922,902 | 5/1990 | Wuchinich et al. | 604/22 |
| 4,983,160 | 1/1991 | Steppe et al. | 604/22 |
| 5,084,009 | 1/1992 | Mackool | 604/22 |

FOREIGN PATENT DOCUMENTS 0269870 10/1987 European Pat. Off. .
0375302 12/1989 European Pat. Off. .
0376562 12/1989 European Pat. Off. .

OTHER PUBLICATIONS

"Scleral and Corneal Burns During Phacoemulsification with Viscoelastic Materials," *ECRI*, 17(12):377–79 (Dec. 1988).

Polack et al., "The Phacoemulsification Procedure, III, Corneal Complications," *Invest. Ophthal. Visual Sci.* 39–46 (1977).

Strobel et al., "Phaco-Emulsification and Planned ECCE: Intraoperative Differences in Intraocular Heating," *Eur. J. Implant, Ref. Surg.* 3:135–38 (1991).

Primary Examiner—Stephen C. Pellegrino
Assistant Examiner—Michael Rafa
Attorney, Agent, or Firm—Jeffrey S. Schira

[57] ABSTRACT

An irrigating sleeve for use in combination with the cutting tip of a phacoemulsification handpiece containing a base having a nose and a hollow interior; a tube connected to the base at the nose having an interior surface, an open end opposite the nose and a longitudinal bore to receive the cutting tip in communication with the hollow interior of the base; and a rough texture comprised of random bumps and pits on the interior surface of the tube for reducing the amount of surface contact between the cutting tip and the interior surface of the tube during tube compression and for bathing the cutting tip continuously in a lubricant.

18 Claims, 2 Drawing Sheets

TEXTURED IRRIGATING SLEEVE

BACKGROUND OF THE INVENTION

The present invention relates to ultrasonic ophthalmic surgical equipment and, in particular, to phacoemulsification, ultrasonic irrigating sleeves and related ultrasonic cutting tips. Ultrasonic irrigating sleeves and ultrasonic cutting tips are critical and principal parts of ultrasonic ophthalmic surgical equipment.

A typical ultrasonic surgical device suitable for ophthalmic procedures consists of an ultrasonically driven handpiece with attached cutting tip and irrigating sleeve and an electronic control console. The handpiece assembly or probe is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced-diameter portion or nosecone at the body's distal end. The nosecone is externally threaded to accept the irrigation sleeve. Likewise, the horn bore is internally threaded at its distal end to receive the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic irrigating sleeves are more fully described in U.S. Pat. Nos. 4,787,889 and 4,808,154, the entire contents of which are incorporated herein by reference.

In use, the ends of the cutting tip and irrigating sleeve are inserted into a small incision of predetermined width in the cornea, or other location. The cutting tip is ultrasonically vibrated within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device on the console. The aspiration of emulsified tissue is aided by a saline flushing solution or irrigant that is injected into the surgical site through the small annular gap between the inside surface of the irrigating sleeve and the cutting tip and by the ports at the distal end of the sleeve.

One concern in phacoemulsification surgical procedures is the problem of heat build-up in the cutting tip. Wound pressure on the irrigating sleeve walls compresses the walls and causes both reduced fluid flow to and from the cutting tip and heat-producing frictional contact between the vibrating cutting tip and the walls of the sleeve. Thus, as cooling fluid flow is diminished, frictional heat increases without a means to dissipate the heat. The heat build-up is sudden and pronounced, and can cause scleral or corneal burns very quickly. This problem becomes increasingly a concern when higher frequency (i.e. higher energy) vibrations are used. Prior art handpiece assemblies (or probes) generally have relied on the flow of the irrigant between the cutting tip and the sleeve and the flow of aspirated material into the cutting tip bore to cool the cutting tip. However, the viscoelastic material injected into the anterior ocular chamber during a typical phacoemulsification procedure resists the flow of the irrigant out of the sleeve and is highly resistant to aspiration flow into the cutting tip bore. Therefore, the flow of aspiration and irrigation fluids into and out of the eye can be momentarily occluded whenever the cutting tip and sleeve contact the viscoelastic material. This momentary occlusion can result in sudden cutting tip overheating and resultant scleral and/or corneal lesions because cutting tip overheating occurs very rapidly (within 1 to 3 seconds) and even short term exposure to such overheating can cause injury to delicate eye tissue.

Prior art sleeves have used a variety of techniques to reduce cutting tip heating. For example, in their U.S. Pat. No. 4,787,889, Steppe, et al. disclose a cutting tip cap and sleeve having a smooth bore. The sleeve disclosed by Steppe, et al. reduces the likelihood of cutting tip overheating because the sleeve is fabricated from a rigid resilient resin that resists collapse or compression due to wound pressure.

In his U.S. Pat. No. 4,808,154, Freeman discloses an aspiration and irrigation sleeve with longitudinal ribs along the sleeve bore. The ribs allow the irrigant to flow more readily out the sleeve even under the restrictive effect of wound pressure on the sleeve wall, thereby enhancing the cooling of the cutting tip. However, the sleeve disclosed by Freeman still relies principally on an unoccluded flow of fluids within the cutting tip and sleeve to cool the cutting tip and does not recognize the need to reduce the amount of friction and the resultant heat build-up in the cutting tip.

BRIEF SUMMARY OF THE INVENTION

The phacoemulsification irrigating sleeve of the present invention improves upon prior art irrigating sleeves by providing a sleeve that more effectively reduces the amount of friction between the cutting tip and the sleeve during sleeve compression than prior art sleeves, thereby reducing heat build-up in the cutting tip. By reducing the tendency of the cutting tip to overheat, the irrigating sleeve of the present invention is not as dependent on fluid flow cooling as are prior art sleeves.

The irrigating sleeve of the present invention reduces the amount of friction between the cutting tip and the sleeve by providing a sleeve with a rough textured or sandpaper-like bore surface. The texturing of the sleeve bore has a number of advantages; it reduces the amount of surface contact between the cutting tip and the sleeve during sleeve wall compression against the vibrating cutting tip due to wound pressure and it allows a small amount of the irrigant to flow through the sleeve at such times, thus lubricating both the cutting tip and the sleeve. By reducing the surface contact between the cutting tip and the sleeve during compression of the sleeve, the amount of heat-generating friction is reduced when the cutting tip is energized. In addition, the small amount of irrigant that is always trapped between the cutting tip and the sleeve, even under the adverse conditions noted above, serves to lubricate the cutting tip, further reducing the amount of friction between the cutting tip and the sleeve.

Accordingly, one objective of the present invention is to provide a phacoemulsification irrigating sleeve that resists heat build-up in the cutting tip.

A further objective of the present invention is to provide a phacoemulsification irrigating sleeve that reduces the amount of friction between the sleeve and the cutting tip during sleeve compression.

Another objective of the present invention is to provide a phacoemulsification irrigating sleeve that continuously lubricates the cutting tip.

Still another objective of the present invention is to provide a phacoemulsification irrigating sleeve with a textured bore.

These and other objectives and advantages of the present invention will become apparent from the drawings, detailed description and claims which follow.

DETAILED DESCRIPTION OF THE INVENTION

Figure 1:
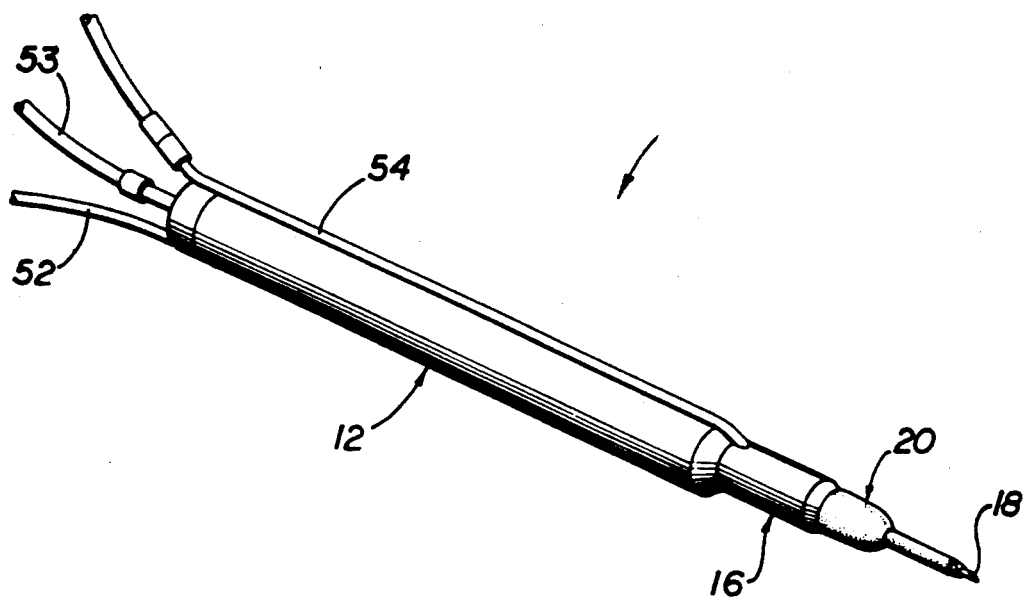
FIG. 1 is a perspective view of a phacoemulsification handpiece incorporating the present invention.
Figure 2:
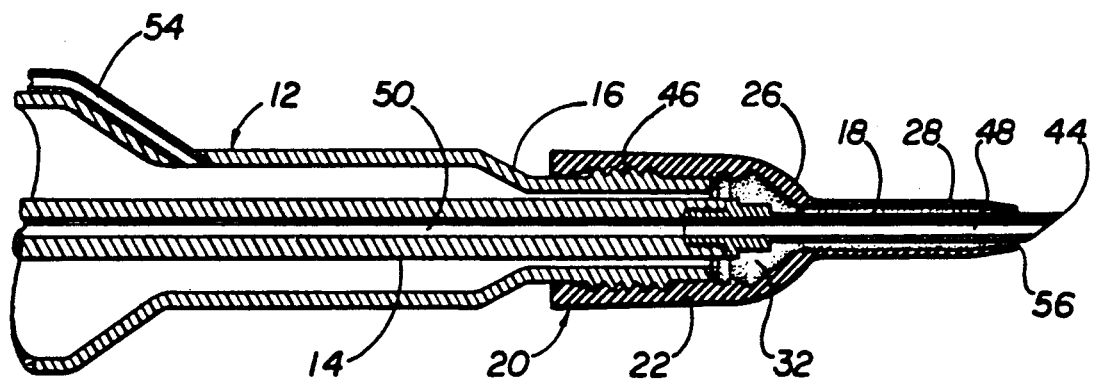
FIG. 2 is an enlarged longitudinal cross section of the distal end of the handpiece assembly illustrated in FIG. 1.

As can be seen in FIGS. 1 and 2, phacoemulsification handpiece assembly 10 generally comprises a hollow handpiece body 12 having an ultrasonically driven horn 14, an electric power supply cord 52, an aspiration line 53, an integral irrigation line 54, a handpiece nosecone 16, a hollow surgical cutting tip 18 and an irrigating sleeve 20. Handpiece body 12, horn 14, nosecone 16 and cutting tip 18 are known in the art and are available from manufacturers such as Alcon Surgical, Inc. and others.

Figure 3:
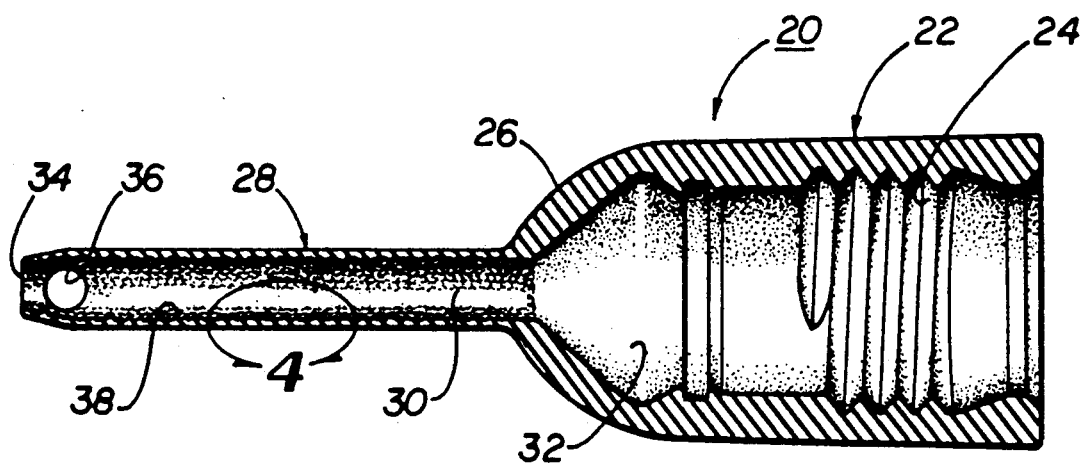
FIG. 3 is a longitudinal cross section of the phacoemulsification irrigating sleeve of the present invention.

As can be seen in FIGS. 1, 2 and 3, sleeve 20 generally comprises a base 22 having a nose 26, a hollow interior 32 with internal threads 24 and a tube 28 connected to base 22 at nose 26 having a distal free end 34 opposite nose 26. A longitudinal bore 30 extends down the length of tube 28 from hollow interior 32 of base 22 to free end 34. Free end 34 of tube 28 contains two or more ports 36 that communicate with bore 30. Sleeve 20 is preferably made from a resilient material such as rubber or thermoplastic with silicone rubber being preferred, but other suitable materials also may be used.

Figure 4:
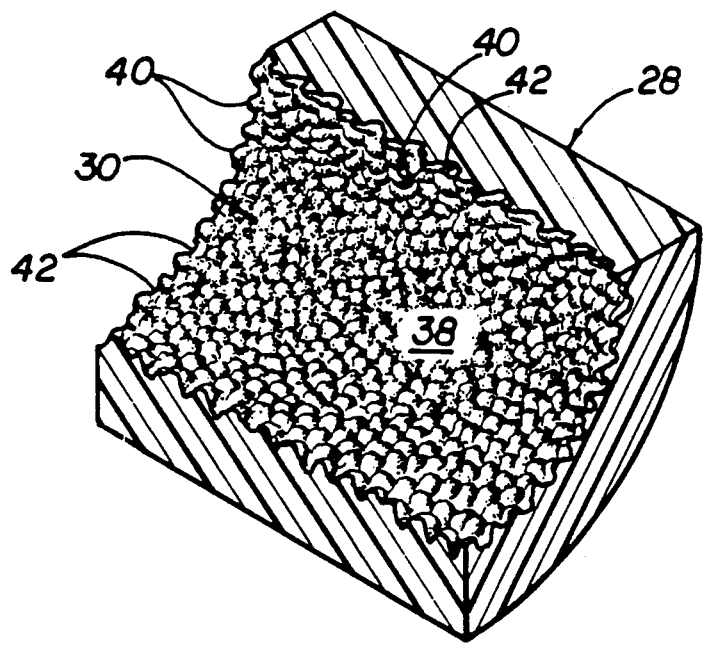
FIG. 4 is an enlarged fragmentary perspective view of the interior surface of the irrigating sleeve illustrated in FIG. 3 taken at circle 4.

As can be seen in FIG. 4, interior surface 38 of tube 28 has a random but uniformly rough texture, giving surface 38 a relieved or sandpaper-like appearance. This texturing preferably consists of random alternating bumps 40 and pits 42 but other suitable textures can also be used. The depth of pits 42 below bumps 40 is not critical, but a depth of approximately 0.001 to 0.003 inches is preferred. Bumps 40 and pits 42 can be formed on surface 38 by acid etching or bead or sand blasting the mold (not shown) used to form sleeve 20 or any other suitable method.

As shown in FIGS. 1 and 2, handpiece assembly 10 is assembled by threading cutting tip 18 on horn 14 in handpiece body 12. Sleeve 20 is telescopically inserted over cutting tip 18 so that distal tip end 44 of cutting tip 18 extends through bore 30 and projects a predetermined distance out free end 34 of tube 28 and internal threads 24 in hollow interior 32 of base 22 are received on external threads 46 on nosecone 16. Handpiece assembly 10 is connected to any suitable conventional phacoemulsification control panel (not shown).

In use, horn 14 is caused to vibrate ultrasonically and these vibrations are transmitted along cutting tip 18 to distal tip end 44 where the vibrations are used to fracture or emulsify a cataract or other tissue (not shown). A reduced pressure source (not shown) draws the emulsified tissue or aspirant through bore 48 in cutting tip 18 and bore 50 in horn 14 and out handpiece assembly 10 through flexible aspiration line 53. An irrigant source (not shown) supplies an irrigant such as saline solution under pressure through irrigation line 54 and handpiece body 12 to the interior 32 of sleeve base 22 where the irrigant is forced to migrate along bore 30 in tube 28 in annular space 56 between cutting tip 18 and interior surface 38 of tube 28. The irrigant exits handpiece assembly 10 out free end 34 of tube 28 and out ports 36.

As can be seen in FIGS. 2 and 4, cutting tip 18 touches interior surface 38 of tube 28 during periods of contact with cutting tip 18 only at bumps 40, thereby reducing the amount of frictional contact area between cutting tip 18 and interior surface 38. In addition, pits 42 continue to retain a small amount of irrigant even if the flow of irrigant is interrupted, thereby continuously bathing cutting tip 18 in the lubricating irrigant.

This description is given for purposes of illustration and explanation. It will be apparent to those skilled in the relevant art that modifications can be made to the invention as described above without departing from its scope or spirit.

We claim:

1. An irrigating sleeve for use in combination with a cutting tip of a phacoemulsification handpiece, comprising:
   a) a base having a nose, a hollow interior and a means for connecting the base to the handpiece;
   b) a tube connected to the base at the nose having an interior surface, an open end opposite the nose and a longitudinal bore in communication with the hollow interior of the base that receives the cutting tip; and
   c) a means for randomly and nonlinearly reducing the amount of surface contact between the cutting tip and the interior surface of the tube during tube compression and for bathing the cutting tip continuously in a lubricant.

2. The irrigating sleeve of claim 1 wherein the reducing and bathing means comprises a rough texture on the interior surface of the tube.

3. The irrigating sleeve of claim 2 wherein the rough texture comprises random bumps and pits.

4. The irrigating sleeve of claim 1 wherein the sleeve comprises a resilient material.

5. The irrigating sleeve of claim 4 wherein the resilient material comprises silicone rubber.

6. The irrigating sleeve of claim 2 wherein the handpiece has a nosecone with external threads and the means for connecting the base to the handpiece comprises internal threads in the hollow interior of the base that are received on the external threads of the nosecone.

7. An irrigating sleeve for use in combination with a cutting tip of a phacoemulsification handpiece having a nosecone with external threads, comprising:
   a) a base having a nose and a hollow, threaded interior that is received on the external threads of the nosecone;
   b) a tube connected to the base at the nose having an interior surface, an open end opposite the nose and a longitudinal bore in communication with the hollow interior of the base that receives the cutting tip; and
   c) a rough texture comprised of random bumps and pits on the interior surface of the tube for randomly reducing the amount of surface contact between the cutting tip and the interior surface of the tube during tube compression and for bathing the cutting tip continuously in a lubricant.

8. The irrigating sleeve of claim 7 wherein a depth of the pits below the bumps is approximately between 0.001 to 0.003 inches.

9. The irrigating sleeve of claim 7 wherein the sleeve comprises a resilient material.

10. The irrigating sleeve of claim 9 wherein the resilient material comprises silicone rubber.

11. A phacoemulsification handpiece comprising:
   a) a handpiece body having a free end;
   b) a cutting tip retained on the handpiece body at the free end;
   c) an elongated sleeve having a longitudinal bore and an interior surface coaxially mounted at the free end so that the cutting tip extends down the bore; and
   d) a means for randomly and nonlinearly reducing the amount of surface contact between the cutting tip and the interior surface of the sleeve during compression of the sleeve and for bathing the cutting tip continuously in a lubricant.

12. The phacoemulsification handpiece of claim 11 wherein the reducing and bathing means comprises a rough texture on the interior surface of the sleeve.

13. The phacoemulsification handpiece of claim 12 wherein the rough texture comprises random bumps and pits.

14. The phacoemulsification handpiece of claim 11 wherein the sleeve comprises a resilient material.

15. The phacoemulsification handpiece of claim 14 wherein the resilient material comprises silicone rubber.

16. The phacoemulsification handpiece of claim 13 wherein a depth of the pits below the bumps is approximately between 0.001 and 0.003 inches.

17. A phacoemulsification handpiece comprising:
   a) a handpiece body having a free end;
   b) a cutting tip retained on the handpiece body at the free end;
   c) an elongated sleeve made from a resilient material having a longitudinal bore and an interior surface coaxially mounted at the free end with the cutting tip so that the cutting tip extends down the bore; and
   d) a rough texture comprised of random bumps and pits on the interior surface of the sleeve for randomly reducing the amount of surface contact between the cutting tip and the interior surface of the bore during compression of the sleeve and for bathing the cutting tip continuously in a lubricant wherein a depth of the pits below the bumps is approximately between 0.001 and 0.003 inches.

18. The phacoemulsification handpiece of claim 17 wherein the resilient material comprises silicone rubber.

* * * * *